United States Patent [19]

Vaughan

[11] 4,409,403

[45] Oct. 11, 1983

[54] OXYALKYLATION PROCESS

[75] Inventor: Ronald J. Vaughan, Orinda, Calif.

[73] Assignee: Varen Technology, Marshallton, Del.

[21] Appl. No.: 306,482

[22] Filed: Sep. 28, 1981

Related U.S. Application Data

[63] Continuation-in-part of Ser. No. 179,520, Aug. 19, 1980, Ser. No. 90,940, Nov. 5, 1979, abandoned, and Ser. No. 660,634, Feb. 23, 1976, Pat. No. 4,317,949, said Ser. No. 179,520, is a continuation-in-part of Ser. No. 65,613, Aug. 9, 1979, abandoned, which is a continuation-in-part of Ser. No. 904,502, May 10, 1978, abandoned, said Ser. No. 90,940, is a continuation-in-part of Ser. No. 660,634, , and Ser. No. 65,613.

[51] Int. Cl.$^3$ ............................................. C07C 41/03
[52] U.S. Cl. ............................ 568/678; 203/DIG. 6;
260/971; 568/607; 568/608; 568/613; 568/614;
568/618; 568/620; 568/648; 568/649; 568/650;
568/651; 568/672; 568/676; 568/679; 568/867
[58] Field of Search ............... 568/607, 608, 613, 614,
568/618, 620, 648, 649, 650, 651, 672, 676, 679,
867, 678; 203/DIG. 6; 260/971

[56] References Cited

U.S. PATENT DOCUMENTS

| | | |
|---|---|---|
| 2,293,868 | 8/1942 | Toussaint . |
| 2,684,387 | 7/1954 | Young . |
| 2,807,651 | 9/1957 | Britton et al. ........................ 568/618 |
| 3,041,317 | 6/1962 | Gibbs et al. . |
| 3,282,875 | 11/1966 | Connolly et al. . |
| 3,624,053 | 11/1971 | Gibbs et al. . |
| 3,882,093 | 5/1975 | Cavanaugh et al. . |
| 3,954,884 | 5/1976 | Kidwell . |
| 4,165,440 | 8/1979 | Kim . |

FOREIGN PATENT DOCUMENTS

| | | |
|---|---|---|
| 37-4308 | 6/1962 | Japan . |
| 38-4858 | 4/1963 | Japan . |
| 49-20166 | 5/1974 | Japan . |
| 52-3923 | 1/1977 | Japan . |

*Primary Examiner*—Howard T. Mars
*Attorney, Agent, or Firm*—Charles J. Tonkin

[57] ABSTRACT

This invention relates to oxyalkylations which take place in the presence of solid acid catalysts. More particularly this invention relates to increasing the selectivity of such processes employing a solid acid catalyst, preferably a polyfluorosulfonic acid catalyst, in which an hydroxylic compound reactant reacts with an alkylene oxide reactant to produce a desired mono-oxyalkylated product which tends to react with the alkylene oxide to produce an undesired second product. The improvement comprises the steps of (1) vaporizing the hydroxylic compound in a reflux zone, (2) passing vaporized hydroxylic compound through a catalyst zone to a condenser wherein vaporized hydroxylic compound is condensed, (3) returning condensed hydroxylic compound to the catalyst zone and in the catalyst zone contacting condensed hydroxylic compound with vaporized hydroxylic compound and the alkylene oxide in the presence of a solid insoluble acidic catalyst at reaction conditions whereby the desired mono-oxyalkylated derivative is formed, (4) passing reaction products and unreacted condensed hydroxylic compound to the reflux zone, and (5) recovering the mono-oxyalkylated derivative.

5 Claims, 1 Drawing Figure

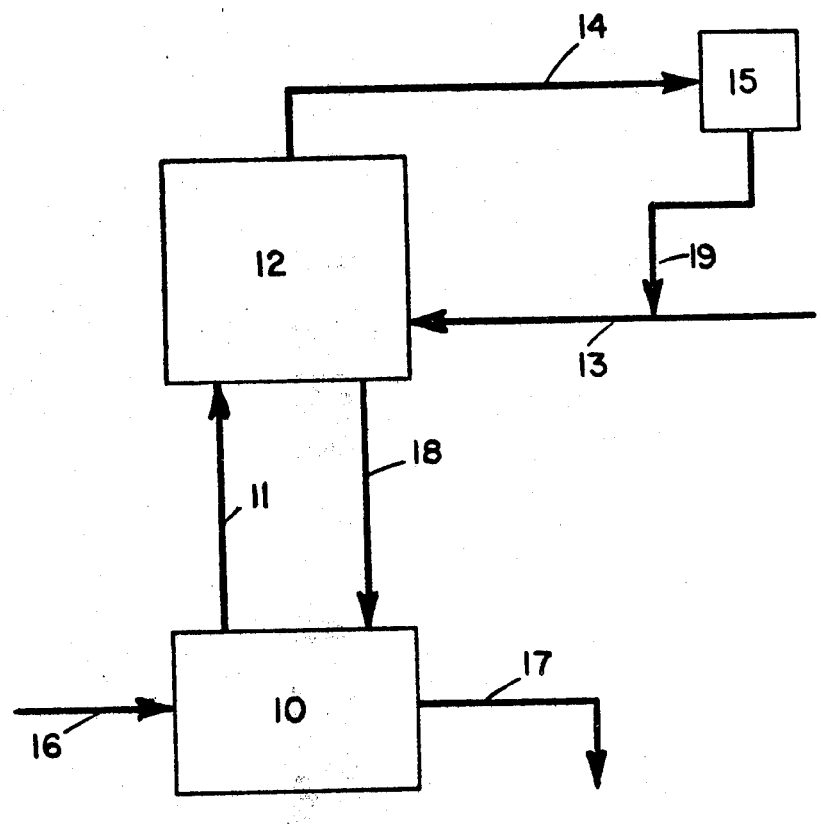

OXYALKYLATION PROCESS

This patent application is a continuation-in-part of U.S. Ser. No. 660,634, filed Feb. 23, 1976 now U.S. Pat. No. 4,317,949; U.S. Ser. No. 090,940, filed Nov. 5, 1979, now abandoned (which is a continuation-in-part of said U.S. Ser. No. 660,634 and U.S. Ser. No. 065,613, filed Aug. 9, 1979, now abandoned which in turn is a continuation-in-part of U.S. Ser. No. 904,502, filed May 10, 1978, now abandoned); and U.S. Ser. No. 179,520, filed Aug. 19, 1980 (which is a continuation-in-part of said U.S. Ser. No. 065,613, now abandoned which in turn is a continuation-in-part of said U.S. Ser. No. 904,502, now abandoned).

FIELD OF THE INVENTION

This invention relates to oxyalkylation processes which take place in the presence of solid acid catalysts, especially polyfluorosulfonic acid catalysts. More particularly, this invention concerns increasing the selectivity of such processes in which an hydroxylic compound reactant reacts with an alkylene oxide in the presence of a solid acid catalyst to produce a desired mono-oxyalkylated product which tends to react with the alkylene oxide to produce a less desirable second product. Usually the monoalkylated product tends not to react with the hydroxylic compound. Usually and preferably the reaction is carried out with an excess of said hydroxylic compound. The reaction products are usually and preferably higher boiling than the hydroxylic compound, sufficiently so that refluxing a mixture of the hydroxylic compound and the products can produce a vaporized hydroxylic compound essentially free of the products but which may contain alkylene oxide. As illustrative of the present invention, improved selectivity for the mono-oxyalkylation product in the oxyalkylation of an hydroxylic compound with an alkylene oxide in the presence of a solid acidic catalyst, preferably a polyfluorosulfonic acid catalyst, is obtained by (1) refluxing a mixture comprising said hydroxylic compound and the oxyalkylated derivative thereof, (2) separating from the mixture of step (1) an overhead product comprising said hydroxylic compound, said overhead product being substantially free from said oxyalkylated derivatives, (3) condensing said overhead product, (4) contacting said condensed overhead product with said alkylene oxide in the presence of a polyfluorosulfonic acid catalyst, at conditions whereby a portion of said hydroxylic compound is reacted to form the oxyalkylated derivative thereof, and (5) returning the resultant mixture of the hydroxylic compound and its oxyalkylated derivative to the refluxing mixture of step (1). Fresh hydroxylic compound may be continuously added to said refluxing mixture while continuously withdrawing said oxyalkylated derivatives.

BACKGROUND OF THE INVENTION

Acid catalyzed reactions such as alkylation usually employs liquid sulfuric acid, hydrogen fluoride, aluminum chloride, and phosphoric acid supported on kieselguhr and sulfonated polystyrene as catalysts, all of which have drawbacks. A stable, solid acid catalyst which is easily separated from the reaction mixture is desirable.

McClure U.S. Pat. Nos. 4,056,578 and 4,022,847 and 4,041,090 refer to conversion processes including alkylation and isomerization, using as a catalyst perfluorinated polymers containing pendant sulfonic acid groups.

Kapura and Gates report in an article "Sulfonated Polymers as Alkylation Catalysts," Industrial Engineering Chemistry Product Research Development, Vol. 12, No. 1, pp. 62–66(1973), on tests of several sulfonated polymers for activity as alkylation catalysts. The alkylation embodiment of the present invention is based upon the finding that substantially higher selectivities are obtained than reported by Kapura and Gates.

The general oxyalkylation reaction is described and claimed in my copending application, Ser. No. 179,520, filed Aug. 19, 1980.

SUMMARY OF THE INSTANT INVENTION

The instant invention relates to a selective oxyalkylation process which is carried out in the presence of a solid acid catalyst, more preferably a perfluorocarbon polymer sulfonic acid catalyst and relates more specifically to reacting an hydroxylic compound reactant with an alkylene oxide reactant to produce a mono-oxyalkylated product which tends to react with the alkylene oxide to produce an undesired second product. The improvement involves bring together, as described more fully hereinbelow, in a catalyst zone, a solid acidic catalyst, a vapor containing the hydroxylic compound reactant and the alkylene oxide and a liquid containing the hydroxylic compound, all at or close to the boiling temperature of the liquid (in the absence of an inert gas) at the operating pressure.

In general, the invention is applicable to oxyalkylations wherein an hydroxylic compound combines with an alkylene oxide to form a mono-oxyalkylated product which may subsequently react with said alkylene oxide to give undesirable impurities. This mode of operation is especially suitable in instances wherein the mono-oxyalkylated product will further react with the alkylene oxide at a greater rate than with the hydroxylic compound. The selectivity to the desired mono-oxyalkylated product is improved by means of the process of the instant invention. Usually and preferably, the mono-oxyalkylated product will have a higher boiling point than the hydroxylic compound. Furthermore, the alkylene oxide preferably has a much lower boiling point (preferably greater than 20° C.) than either said hydroxylic compound or said mono-oxyalkylated product, i.e., so that it will not be returned in its unreacted form to the refluxing mixture. In general, any difference in boiling point of, for example, at least 5° C. between the mono-oxyalkylated product and the hydroxylic compound is suitable for carrying out the process of this invention. Preferably, the mono-oxyalkylated product will have a boiling point at least 10° C. greater than the boiling point of the hydroxylic compound.

BRIEF DESCRIPTION OF DRAWING

The details of the present invention will be described in connection with the accompanying drawing which is a schematic flow diagram of how the process is carried out as applied to oxyalkylation reactions wherein the mono-oxyalkylate is the desired product.

DETAILED DESCRIPTION OF THE INVENTION

The improved process of the present invention for reacting an hydroxylic compound reactant with an alkylene oxide reactant to produce the desired mono-oxyalkylated product which tends to react with the alkylene oxide to produce an undesired second product, i.e., impurity, comprises the improvement of:

(1) vaporizing the hydroxylic compound in a reflux zone, (2) passing vaporized hydroxylic compound through a catalyst zone to a condenser wherein the vapor is condensed, (3) returning condensed hydroxylic compound to the catalyst zone and in the catalyst zone contacting condensed hydroxylic compound with a mixture of the vaporized hydroxylic compound and vaporized alkylene oxide in the presence of a solid insoluble acid catalyst, preferably a perfluorocarbon polymer sulfonic acid catalyst, at reaction conditions whereby the desired mono-oxyalkylated product is formed, (4) passing reaction products and unreacted condensed hydroxylic compound to the reflux zone, and (5) recovering the desired mono-oxyalkylated product.

Generally the reactants will have boiling temperature at the operating pressure in the temperature range below that at which the catalyst is adversely effected such as by softening, decomposing or inactivated to a substantial degree, i.e. becomes unstable. Thus this maximum temperature is determined by the catalyst selected; particularly for the preferred perfluorocarbon polymer sulfonic acid catalyst the maximum temperature is 230° C.; generally the temperature is more preferably below 200° C.

By operating in the above described manner, it is evident that the catalyst zone is maintained at the boiling temperature of the liquid phase containing the highest boiling reactant. The higher boiling product will accumulate in the pot of the reflux zone or can be removed at some intermediate point. Thus, the catalyst zone will have three phases, namely a solid acid catalyst in equilibrium or saturated with a liquid phase, liquid phase usually saturated with the higher boiling reactant in equilibrium with vapor enriched with the lower boiling second reactant. By thus obtaining equilibrium between the liquid and vapor phases in the catalyst zone, the temperature is under microscopic control at the catalyst sites whereby heat of reaction is converted to heat of vaporization in the catalyst zone and thereby the heating economy is improved and localized hot spots are minimized.

REACTION CONDITIONS

The reaction conditions are selected within the criteria of the above defined process to promote the desired mono-oxyalkylation. For example, temperatures of from 0° C. to 200° C. and pressure of from 0 psig to 1000 psig may be conveniently used although the specific operating pressures will relate to the specific compounds which are to be used. In general, the pressure can be adjusted to assist in maintaining the vapor and liquid phases as described above. The temperature can be adjusted by application of vacuum or addition of an inert gas. The feed rates are adjusted so as to provide a high conversion, preferably substantially complete conversion, in the time of passage of the alkylene oxide through the catalyst zone.

THE CATALYST

The preferred polyfluorosulfonic acid catalyst which is used in the process of the instant invention is a fluorocarbon polymer containing pendant sulfonic acid groups and may be derived from fluorocarbon polymers having mixed chlorine and fluorine substituents, wherein the number of chlorine atoms is not more than about 20% of the total chlorine and fluorine atoms present in said polymer. The perfluorinated derivatives of these materials are particularly useful in the process of the instant invention and said perfluorocarbon polymer may have the pendant sulfonic acid attached either directly to the main polymer chain or to perfluorocarbon side chains which are attached to the main polymer chain. Either or both of the main polymer chain and the side chain may contain oxygen atom linkages, such as ether linkages, for example, as in Nafion TM, a perfluorosulfonic acid polymer obtained from E. I. duPont de Nemours and Company (see the description given in Innovation, Vol. 4, No. 3, (1973), pp. 10–13). The perfluorocarbon polymer particularly useful in the present invention may be prepared as disclosed in U.S. Pat. Nos. 3,041,317; 3,282,875; and 3,624,053, hereby incorporated by reference. The most preferred polymers are prepared by copolymerizing a perfluorovinyl ether having the formula:

$$FSO_2CF_2OCF(CF_3)CF_2OCF{=}CF_2$$

and tetrafluoroethylene followed by conversion of the $SO_2F$ groups to sulfonic acid groups. The equivalent weight of the preferred copolymer preferably ranges from 850 to 2500 where the equivalent weight is defined as the average molecular weight per sulfonyl group.

The above catalyst may be used in the process of the instant invention in various physical forms, that is it may be fabricated into sheets, hollow tubes, granules having a particle size of from 6 mesh to less than 400 mesh (preferably 10 to 200 mesh), fibers, etc. The catalyst may be used in a supported or unsupported manner, e.g., the catalyst can be coated onto a metal or other substrate, as further described below. The catalyst can be particulated or formed into other shapes such as tubes and fibers and arranged such as in beds of granules, for the convenient passing therethrough of upflowing vapor and downflowing liquid with intimate contact of the vapor and liquid and the catalyst as is well known in the art. The catalyst can be arranged as a fluid bed or supported on sieve trays. It is important to note that the preferred fluorocarbon sulfonic acid catalyst of the instant invention is insoluble in, and inert to deactivation by the various reactant mixtures, at the conditions at which the process is carried out, thus providing ease of separation and generally longer cataylst life as compared to various solid and liquid catalysts, such as sulfonated polystyrene, sulfuric acid, HF, and phosphoric acid supported on kieselguhr. Generally, other insoluble, solid sulfonated or other acid catalysts can be used.

For example, the sulfonated polystyrene catalysts such as those described in U.S. Pat. Nos. 3,037,052; 3,017,441 and 3,239,575 can be used in the present process; however, they are generally less stable and hence are less preferred than the perfluorocarbon polymer sulfonic acid catalysts described above.

It is noted that the skilled artisan may make various variations on this preferred mode of operation, all of which are within the spirit of the instant invention. For example, the hydroxylic compound may be condensed in the same zone in which the solid acid catalyst is contained or may be condensed in a tower at a point located above the solid acid catalyst and fed by gravity to the catalyst zone.

The present invention is further illustrated by the following. Referring to the schematic flow diagram of the drawing, a mixture of the hydroxylic compound which is to be oxyalkylated and various oxyalkylated derivatives thereof are refluxed in zone 10. An overhead product comprising the hydroxylic compound, said overhead being substantially free of the oxyalkylated derivatives is separated from the mixture and led through conduit 11 into zone 12 wherein it is condensed. The alkylene oxide is brought into zone 12 through line 13 and contacted therein with the condensed overhead product in the presence of the catalyst, preferably the perfluorocarbon polymer sulfonic acid catalyst described above. Conditions are maintained in zone 12 sufficient to convert at least a portion of the hydroxylic compound present in said condensed overhead product to the mono-oxyalkylated derivative thereof. The mono-oxyalkylated derivative may be returned via conduit 18 along with the unconverted hydroxylic compound to zone 10. The unreacted alkylene oxide is passed through conduit 14 into zone 15 wherein it may be recovered and recycled via conduit 19 to zone 12. In one preferred embodiment of the process of the instant invention, fresh hydroxylic compound is continuously added through line 16 to zone 10 while a fraction containing a substantially high amount of the oxyalkylated derivatives of said hydroxylic compound is withdrawn through conduit 17. When operating in this manner, the following advantages are obtained. An hydroxylic compound essentially free of its higher boiling oxyalkylated derivatives is continuously contacted with the alkylene oxide stream in zone 12. Thus, the selectivity to the mono-oxyalkylated product is increased.

The hydroxylic compounds that can be oxyalkylated include any organic compounds containing one or more hydroxy (—OH) groups. Water is also included within the scope of the term hydroxylic compound. Certain of the hydroxylic compounds contemplated for use within the scope of this invention may also be described by the formulas

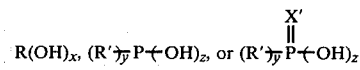

wherein R is hydrogen or hydrocarbyl, R' is hydrocarbyl, hydrocarbyl —X'—, or hydrogen, X' is oxygen or sulfur, x is an integer, preferably of 1 to 6, with the proviso that when R is hydrogen, x is one, z is an integer from 1 to 3, and y is 3-z. Of particular interest are those hydroxylic compounds wherein R is hydrogen, alkyl of 1-20 carbon atoms, phenyl, alkylphenyl of 7 to 30 carbon atoms, hydroxyalkyl of 2 to 20 carbons, or hydrocarbyloxyalkyl of the formula hydrocarbyl ─(O─alkyl)$_g$ where the hydrocarbyl group contains 1-20 carbon atoms, alkyl is ethylene or propylene and g is at least one.

The hydrocarbyl portion of the hydroxylic compound may be aliphatic, cycloaliphatic, aromatic, or a combination of two or more types of hydrocarbon groups. The hydrocarbyl radical may contain any substituents that do not react with the alkylene oxide under the reaction conditions of the instant invention more readily than does a hydroxyl group. The substituents on the hydrocarbyl group also should not be of a type that might poison the catalyst. Substituent groups that should be avoided can be readily determined by one skilled in the art. Typical of such groups are amino, mercapto, and metal carboxylate. Substituent groups that may be present on the hydrocarbyl portion of the hydroxylic compound without affecting the oxyalkylation reaction include nitro, hydrocarbyloxy, halo, phosphonate, phosphate,

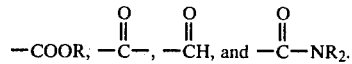

The R group is preferably a straight or branched-chain alkyl of 1 to 20 carbon atoms, H or phenyl.

Particularly preferred hydroxylic compounds are water, methanol, ethanol, 1-dodecanol, 1-butanol, isobutanol, ethylene glycol, glycerol, pentaerythritol, sorbitol, phenol, and alkylated phenols.

The alkylene oxides intended for use within the scope of this invention fall within the general formula

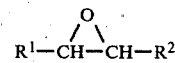

wherein each of $R^1$ and $R^2$ is hydrogen or hydrocarbyl of 1 to 20 carbon atoms or $R^1$ and $R^2$ together with the two carbon atoms form a five- or six-membered cycloaliphatic ring. Other cyclic ethers having four- to six-membered rings can also be used.

Typical alkylene oxides contemplated for use within the scope of this invention are ethylene oxide, propylene oxide, 1,2-butylene oxide, 2,3-butylene oxide, 1,2-pentylene oxide, 2,3-pentylene oxide, 1,2-hexylene oxide, 3-methyl-1,2-pentylene oxide, 2,3-octyleneoxide, 4-methyl-2,3-octylene oxide, 4-methyl-1,2-hexylene oxide, 3-methyl-1,2-butylene oxide, trimethylene oxide and tetrahydrofuran. Because of their commercial availability, ethylene oxide and propylene oxide are preferred. Ethylene oxide is particularly preferred.

The general conditions of oxyalkylation are found in the following, which are incorporated by reference and by way of background: "Catalytic Hydration of Ethylene Oxide" by L. M. Reed, L. A. Wengel and J. B. O'Hara, Industrial and Engineering Chemistry, Vol. 48, pp. 205–208 (February, 1956); "Glycol Production - Hydration of Ethylene Oxide" by D. F. Othmer and M. S. Thakar, Industrial Engineering Chemistry, Vol. 50, pp. 1235–1244 (September, 1958); Toussaint U.S. Pat. No. 2,293,868; Young U.S. Pat. No. 2,684,387; Kidwell U.S. Pat. No. 3,954,884; and Japanese Pat. Nos. 38-4858 (4/63), 37-4308 (6/62), 49-20166 (5/74 and 52-3923 (1/77).

Reaction conditions for conducting oxyalkylation in the process of this invention are within the general criteria set forth hereinabove. Thus the temperature and pressure of the reaction zone are maintained so as to promote the production of the desired product, namely, the product having only one oxyalkyl group per hydroxylic group in the hydroxylic compound. In most oxyalkylations, the temperature is maintained usually between 0° C. and 150° C. The molar ratios of reactants necessary to favor the desired product will be readily apparent to one skilled in the art.

The operation of the preferred steady-state method can be described as follows. The hydroxylic compound is heated to vaporization in a reflux zone. This vaporized mixture then passes through the catalyst zone to a condensing zone where the vaporized mixture becomes liquid and returns to the catalyst zone where it contacts vaporized hydroxylic compound, alkylene oxide and the solid acidic catalyst. The alkylene oxide may be introduced into the reflux zone, the condensing zone, or the catalyst zone.

When the hydroxylic compound and the alkylene oxide come into contact in the catalyst zone, a monoalkylated hydroxylic compound is formed. The monooxyalkylated derivative then returns (as a mixture with unreacted hydroxylic compound) to the reflux zone where it is recovered by fractionation of the mixture of hydroxylic compound and mono-oxyalkylated derivative thereof (the unreacted hydroxylic compound being sent overhead to the catalyst zone).

A mono-oxyalkylated hydroxylic compound essentially free of polyoxyalkylated derivatives can be continuously prepared by the above method. By using the process of this invention for oxyalkylation, monooxyalkylated hydroxylic compounds can be prepared with up to 99 percent or greater selectivity.

The following examples are presented for the purpose of illustrating the oxyalkylation reactions.

EXAMPLE 1

Reaction of Ethylene Oxide With Water in Integrated Reactor-Fractionator

The bulbs of an eight-bulb Allihn condenser evacuated in the outer jacket were packed loosely with wads of wet Nafion TM fibers (9.8 g total, wet) which had been converted to the hydrogen form by treating at 80°–100° C. with 70% nitric acid and washing with water until the wash water was neutral. This catalyst section was fitted atop a reflux-fractionator apparatus which consisted of (in ascending order): a 500 ml r.b. flask with thermometer side arm, a 30×2 cm vigreaux column, insulated, and a short connecting tube with a side arm. A reflux condenser and bubbler were connected to the top of the catalyst section to observe any exit gas flow and to return reactants to the catalyst section. The flask was charged with 100 ml of water, 50 mg of NaHCO₃, and a few boiling chips. Reflux was established through the catalyst section, then ethylene oxide was introduced through the side arm into the tube below the catalyst section. Flow was maintained at 30 ml/min for 18 hours, then increased to 60 ml/min for 2 hours, and then to 80 ml/min for 7.5 hours. The ethylene oxide flow was terminated overnight while reflux was maintained. The ethylene oxide flow was resumed at 80 ml/min for an additional 8 hours; the reaction was terminated at a boiling temperature of 197° C. (730 mm) of the flask contents. Most of the pot contents (340.0 g) were distilled through a 30×1 cm vigreaux column to yield the results shown in Table I-A (Example 1-A).

TABLE I-A

| | | Product of Example 1-A | | | |
|---|---|---|---|---|---|
| Fraction | $T_{head}$(°C.) | $T_{pot}$(°C.) | wt(g) | % | Remarks |
| 1 | 99–195.5 | 193–202 | 3.4 | 1.0 | |
| 2 | 195.5–201 | 202–245 | 230.0 | 68.0 | HOCH₂CH₂OH |
| 3 | 201–242 | 245–255 | 7.6 | 2.2 | |
| 4 | 242–247.5 | 255–275 | 40.5 | 12.0 | HOCH₂CH₂OCH₂CH₂OH |
| 5 | 247.5–256 | 275– | 15.6 | 4.6 | |
| Residue | | | 41.1 | 12.1 | |

The high oligomer (n>1) content of the distillate in I-A prompted a brief inventigation of the effect of ethylene oxide flow rate and efficiency of the fractionating column.

After removal of the pot contents of the reactor-fractionator from the experiment above, the catalyst section was washed by refluxing with fresh water in the pot for 1 hour; the pot contents were removed and replaced with 100 ml of fresh distilled water containing 50 mg of NaHCO₃. Reflux was again established and ethylene oxide was introduced at a flow rate of 16 ml/min for 150 hours. The boiling temperature of the pot contents was then 183° C. (730 mm Hg). A small sample was removed for analysis and the remainder of the pot contents (314.3 g) was distilled (730 mm Hg) through a 1×30 cm vigreaux column to yield the results shown in Table I-B (Example 1-B).

TABLE I-B

| Fraction | $T_{head}$(°C.) | $T_{pot}$(°C.) | wt(g) | % | Remarks |
|---|---|---|---|---|---|
| 1 | 98–186 | 156–195 | 16.1 | 5.1 | |
| 2 | 186–193 | 195–197 | 6.3 | 2.0 | |
| 3 | 193–200 | 197–218 | 254.5 | 81.1 | HOCH₂CH₂OH |
| 4 | 200–241 | 218–248 | 13.4 | 4.2 | |
| 5 | 241–253 | 248–305 | 16.3 | 5.2 | HOCH₂CH₂OCH₂CH₂OH |
| 6 | 253–266 | 305–320 | 2.1 | 0.7 | |
| Residue | | | 4.7 | 1.5 | |

The catalyst section was again washed as above; the vigreaux column used in the reactor-fractionator was replaced by a 30×2 cm vacuum-jacketed fractionating column packed with stainless steel helices. Reflux was established using 50 ml of distilled water and 50 mg of NaHCO₃ in the pot. Ethylene oxide was introduced at a flow rate of 10–14 ml/min. and continued until the pot contents had reached a boiling temperature of 195° C. (730 mm Hg). Gas chromatography of the neat pot contents (on a Carbowax 20M column) revealed only traces of diethylene glycol; the sole organic peak (>99%) was ethylene glycol.

Control (without catalyst)

The reactor-fractionator above was charged with 100 ml of water, 50 mg NaHCO₃ and boiling chips. The catalyst section was replaced by an identical Allihn condenser (evacuated outer jacket) without the Nafion TM fiber catalyst. Reflux was established through this section, then ethylene oxide was introduced at 15 ml/min. Although little gas was observed escaping through the bubbler initially, rapid gas flow was established within an hour. Ethylene oxide flow was continued for 6 hours. The contents of the pot showed a weight loss of 2.1 g and only minute traces of organic materials, primarily ethylene glycol, on gas chromatography.

EXAMPLE 2

Reaction of Ethylene Oxide With Methanol in Integrated Reactor-Fractionator

A bundle of parallel Nafion TM fibers (0.006" diameter, 45 fibers 180 cm long, suspended from their midpoint, 4.48 g total weight) was fitted inside a straight tube condenser and the outer jacket was evacuated. The catalyst was prepared as described in Example 1 and the assembled reactor-fractionator (with the stainless-steel helice-packed fractionator) brought up to reflux with methanol to equilibrate the catalyst. The reactor was cooled and allowed to drain; the pot contents were replaced with 80.1 g of fresh methanol containing 50 mg of $NaHCO_3$. After establishing reflux through the catalyst section, ethylene oxide was introduced at 100–200 ml/min. over a period of 8.24 hours. When the boiling temperature of the pot contents reached 126.5° C. (730 mm Hg) the reaction was halted and the reactor allowed to drain down. A portion (202.1 g) of the pot contents (203.6 g) was distilled (730 mm Hg) through a 30×1 cm vacuum-jacketed vigreaux column to yield the results shown in Table II-A.

TABLE II-A

| Fraction | $T_{head}$(°C.) | $T_{pot}$(°C.) | net wt(g) | % of product | Remarks |
|---|---|---|---|---|---|
| 1 | 65–122 | 124–125 | 7.2 | 3.6 | |
| 2 | 122–124.5 | 125–198 | 173.5 | 85.8 | $CH_3OCH_2CH_2OH$ |
| 3 | 124.5–191 | 198–199 | 0.8 | 0.4 | |
| 4 | 191–194 | 199–262 | 14.1 | 7.0 | $CH_2O(CH_2CH_2O)_2H$ |
| Residue | | | 5.4 | 2.5 | |

A second preparation using an ethylene oxide flow of 15–20 ml/min. required a correspondingly longer time (46 hours) to complete the reaction; gas chromatographic analysis (on a Carbowax 20M column showed the only organic product to be 2-methoxyethanol with a trace of methanol remaining.

EXAMPLE 3

Reaction of Ethylene Oxide With Ethanol in the Integrated Reactor-Fractionator

The catalyst section and reactor-fractionator were prepared as in Example 2 and equilibrated with ethanol under reflux. The pot contents were replaced with 70.4 g of fresh absolute ethanol and reflux was established through the catalyst section. Ethylene oxide was introduced at a flow rate of 15–25 ml/min. for a period of 32 hours; the boiling temperature of the pot contents rose to 132° C. (730 mm Hg). A small sample of the pot contents (133.5 g total) was removed for analysis; the remainder (132.1 g) was distilled (730 mm) through a 30×1 cm vacuum-jacketed vigreaux column to yield the results shown in Table III.

TABLE III

| Fraction | $T_{head}$(°C.) | $T_{pot}$(°C.) | net wt(g) | % of product | Remarks |
|---|---|---|---|---|---|
| 1 | 76.5–126 | 117–135 | 11.0 | 8.3 | |
| 2 | 126–133 | 135–136 | 2.4 | 1.8 | |
| 3 | 133–136 | 136–195 | 108.1 | 82.4 | $CH_3CH_2OCH_2CH_2OH$ |
| 4 | 136–189 | 195–279 | 5.5 | 4.2 | |
| Pot Residue | | | 1.0 | 2.8 | |

I claim:

1. In a process for the oxyalkylation of a vaporizable hydroxylic compound with an alkylene oxide, said reaction being carried out with an excess of said hydroxylic compound and wherein the reaction products are higher boiling than said reactants, the improvement which comprises (1) vaporizing said hydroxylic compound in a reflux zone, (2) passing said vaporized hydroxylic compound through a catalyst zone to a condensing zone whereby said vapor is condensed, (3) returning said condensed hydroxylic compound to said catalyst zone, (4) in said catalyst zone contacting said condensed hydroxylic compound with vaporized hydroxylic compound and an alkylene oxide in the presence of a solid insoluble acid catalyst at about the boiling temperature of the liquid phase containing said hydroxylic compound whereby a mono-oxyalkylated derivative of said hydroxylic compound is formed, (5) returning said mono-oxyalkylated derivative and unreacted hydroxylic compound to said reflux zone, and (6) recovering said mono-oxyalkylated derivative from said reflux zone.

2. The process of claim 1 wherein said first reactant is a hydroxylic organic compound and said second reactant is an alkylene oxide of two to three carbon atoms.

3. The process of claim 1 wherein said hydroxylic compound is an aliphatic alcohol, an aromatic alcohol, an oxyalkylated aliphatic alcohol or an oxyalkylated aromatic alcohol, said alkylene oxide is ethylene oxide or propylene oxide, and said perfluorocarbon polymer contains the repeating structure

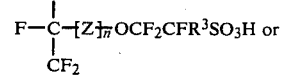

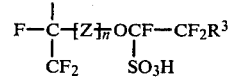

where n is 0, 1 or 2, $R^3$ is fluorine or perfluoroalkyl of 1 to 10 carbon atoms, Z is $-O-CF_2(CF_2-)_m$, $-OCF_2$-

CFY—, or —OCFYCF$_2$—where m is an integer from 1 to 9 and Y is fluorine or trifluoromethyl.

4. The process of claim 1 wherein said hydroxylic compound has the formula ROH where R is hydrogen, alkyl of 1 to 20 carbon atoms, phenyl, alkylphenol of 7 to 30 carbon atoms, hydroxyalkyl of 2 to 20 carbon atoms or hydrocarbyloxy alkyl of the formula hydrocarbyl $-(-O-(CH_2)_q-)_p$ where the hydrocarbyl group contains 1 to 20 carbon atoms, q is 2 or 3, and p is an integer of at least 1.

5. The process of claim 4 wherein said alkylene oxide is ethylene oxide, said perfluorocarbon polymer is a copolymer of tetrafluoroethylene and a perfluorovinyl ether containing pendant sulfonic acid groups, and said hydroxylic compound is water, methanol or ethanol.

* * * * *